United States Patent [19]
Barrabee et al.

[11] Patent Number: 5,618,809
[45] Date of Patent: Apr. 8, 1997

[54] INDOLOCARBAZOLES FROM SACCHAROTHRIX AEROCOLONIGENES COPIOSA SUBSP. NOV SCC 1951 ATCC 53856

[75] Inventors: Ellen B. Barrabee, Fanwood; Ann C. Horan, Summit; Frank A. Gentile, Wayne; Mahesh G. Patel, Verona, all of N.J.

[73] Assignee: Schering Corporation, Kenilworth, N.J.

[21] Appl. No.: 394,937

[22] Filed: Feb. 27, 1995

Related U.S. Application Data

[63] Continuation of Ser. No. 451,487, Dec. 14, 1989, abandoned.

[51] Int. Cl.$^6$ .................. C07D 498/22; A61K 31/55
[52] U.S. Cl. .................. 514/211; 514/410; 540/545; 548/416
[58] Field of Search .................. 540/545; 548/416; 514/211, 410

[56] References Cited

U.S. PATENT DOCUMENTS

| | | | |
|---|---|---|---|
| 4,107,297 | 8/1978 | Omura et al. | 424/122 |
| 4,735,939 | 4/1988 | McCoy et al. | 514/211 |
| 4,923,986 | 5/1990 | Murakata et al. | 540/545 |
| 5,093,330 | 3/1992 | Caravatti et al. | 514/211 |

FOREIGN PATENT DOCUMENTS

| | | | |
|---|---|---|---|
| 1751/88 | 12/1988 | Australia . | |
| 0296110 | 12/1988 | European Pat. Off. | 540/545 |
| 0303697 | 2/1989 | European Pat. Off. . | |
| 0323171 | 7/1989 | European Pat. Off. | 540/545 |
| 0328000 | 8/1989 | European Pat. Off. . | |
| 0383919 | 8/1990 | European Pat. Off. . | |
| 62-120388 | 6/1987 | Japan | 540/545 |
| 62-240689 | 10/1987 | Japan | 540/545 |
| 63-295588 | 12/1988 | Japan | 540/545 |
| 63-295589 | 12/1988 | Japan | 540/545 |
| 0143877 | 6/1989 | Japan | 540/545 |

OTHER PUBLICATIONS

Tanida et al. The Journal of Antibiotics (Nov. 1989) vol. XLII No. 11) pp. 1619–1630.
Tamaoki, et al., Biochemical & Biophysical Research Comm., 135, (1986): pp. 397–402.
Hughes, et al., Tetrahedron Letters, 24, (1983), pp. 1441–1444.
Joyce, et al., Journal of Org. Chem., 52, (1987), pp. 1177–1185.
CA. 107:236750y (1987), Hirata, et al.
CA. 107:236751z (1987), Hirata, et al.
Tanida J. of Antibiotics, XLII(11) 1619 (1989).

Primary Examiner—Robert Gerstl
Attorney, Agent, or Firm—Thomas D. Hoffman

[57] ABSTRACT

N-alkanoyl derivatives of staurospodne represented by the formula I

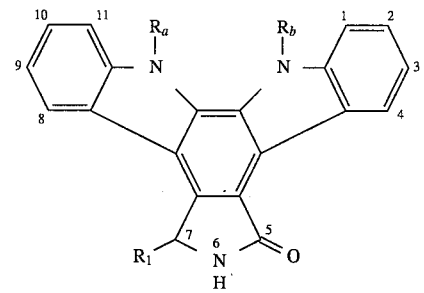

wherein $R_a$ and $R_b$ are each H or

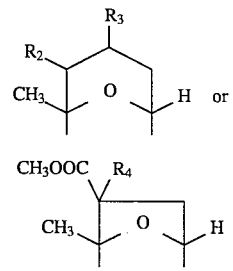

wherein $R_1$ and $R_2$ are independently H or —OH or —OCH$_3$ and $R_3$ is OH, NHCH$_3$, NCH COCH$_3$ or NHCOCH$_3$ and $R_4$ is OH or H and, stereochemical isomers thereof with the provisos that (1) when $R_a$ and $R_b$=A, and $R_1=H_2$ or OH $R_3$ is not NHCH$_3$; (2) when $R_a$ and $R_b$=B, then $R_1=R_4$=OH or $R_1=R_4$=H; (3) when $R_a=R_b$=H $R_1$=—OCH$_3$, and (4) when $R_a$ and $R_b$=A, and $R_1$=H and $R_2$=OCH$_3$, then R3 is not and

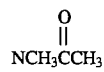

pharmaceutical compositions thereof useful for inhibiting myosin light chain kinase, protein kinase C or tumor cell proliferation as well as producing an antihypertensive effect and an anti-inflammatory effect in warm-blood animals such as man are disclosed.

9 Claims, No Drawings

INDOLOCARBAZOLES FROM SACCHAROTHRIX AEROCOLONIGENES COPIOSA SUBSP. NOV SCC 1951 ATCC 53856

CROSS-REFERENCE TO RELATED APPLICATION

This is a continuation of application Ser. No. 07/451,487, filed Dec. 14, 1989, abandoned. This application is related to a commonly-owned invention by the same inventors U.S. patent application Ser. No. 07/451,271, filed Dec. 14, 1989 which is directed to N-alkanoylstaurosporine derivatives, especially-N-acetylstaurospodne which are isolated from *Saccharothrix aerocolonigenes* subsp. *copiosa* subsp. nov. SCC 1951, ATCC 53856.

BACKGROUND

This invention relates to indolocarbazoles, excluding the N-alkanoylstaurosporine derivatives, isolated from an antibacterial/antifungal complex produced by fermentation of a biologically pure culture of *Saccharothrix aerolonigenes* subsps. *copiosa* subsp. nov. SCC 1951, ATCC 53856. The indolocarbazoles of this invention exhibit selective pharmacological activities, for example in cardiovascular disorders, especially anti hypertensive activity, against proliferation of tumor cells, on inflammation as well as on microbial infections such as caused by bacteria or fungi.

Various indolocarbazoles are known. The indolocarbazole, staurosporine (AM-2282) is disclosed in U.S. Pat. No. 4,107,297 as having antibiotic activity in yeast and fungi as well as having a therapeutic effect on hypertension, edema and ulcers. The indolocarbazoles, TAN-999 and TAN-1030A isolated from culture broths of *Nocardiopsis dassonvillei* and Streptomyces sp as well as the N-acetyl derivative of the amino-derivative of TAN-1030A are disclosed by diseases in which the inhibition of protein kinase C is of importance in a warm blooded animal as well as can be employed as medicaments for tumor-inhibition, inflammation-inhibition, immunomodulation and also in preparations for combating bacterial infections, arteriosclerosis, as well as other diseases of the cardiovascular system and of the central nervous system.

SUMMARY OF THE INVENTION

The present invention provides a compound represented by the formula I:

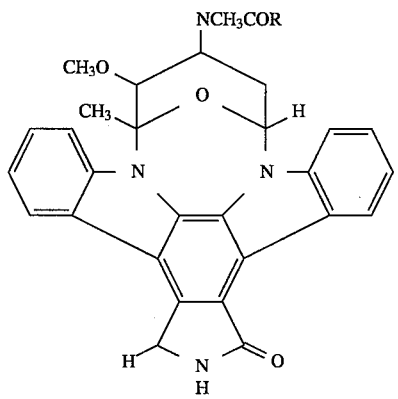

wherein R is a straight or branched chain ($C_1$-$C_9$) alkyl group and stereo-chemical isomers thereof or a pharmaceutically acceptable acid addition salt thereof. The present invention also provides a pharmaceutical composition comprising an effective amount of a compound of formula I and a pharmaceutically acceptable carrier. The pharmaceutical composition of this invention may be administered to warm-blooded animals to inhibit myosin light chain kinase, protein kinase C or tumor cell proliferation or to produce an anti-hypertensive effect or an anti-inflammation effect.

The present invention still further provides a method of treating a warm-blooded animal afflicted by hypertension, which

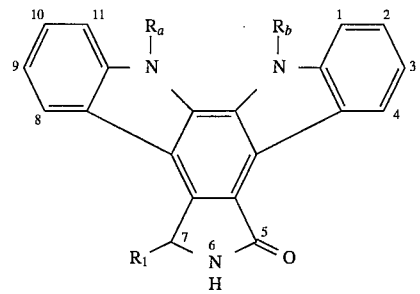

wherein $R_a$ and $R_b$ are each H or

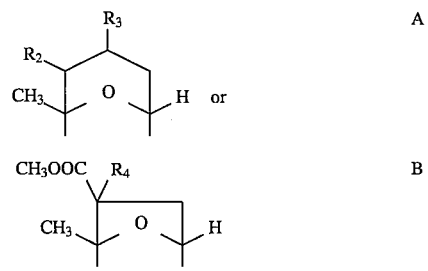

wherein $R_1$ and $R_2$ are independently H or —OH or —OCH$_3$ and $R_3$ is OH, NHCH$_3$, NCH$_3$ COCH$_3$ or NHCOCH$_3$ and $R_4$ is OH or H, and stereochemical isomers thereof with the provisos that (1) when $R_a$ and $R_b$=A, and $R_1$=H or OH, $R_3$ is not NHCH$_3$; (2) when $R_a$ and $R_b$=B, then $R_1$=$R_4$=OH or $R_1$=$R_4$=H; (3) when $R_a$=$R_b$=H, then $R_1$=—OCH$_3$; and (4) when $R_a$ and $R_b$=A, and $R_1$=H, and $R_2$=OCH$_3$, then $R_3$ is not

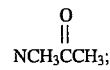
NCH$_3$CCH$_3$;

stereo-chemical isomers thereof or a pharmaceutically acceptable acid addition salt thereof. The present invention also provides a pharmaceutical composition comprising an effective amount of a compound of formula I and a pharmaceutically acceptable carder. The pharmaceutical composition of this invention may be administered to warm-blooded animals to inhibit myosin light chain kinase, protein kinase C or tumor cell proliferation or to produce an anti-hypertensive effect or an anti-inflammation effect.

The present invention still further provides a method of treating a warm-blooded animal afflicted by hypertension, which comprises administering to said animal a therapeutically effective amount of a compound represented by formula I sufficient to treat hypertension or a pharmaceutical composition thereof.

In addition, the present invention provides a method of inhibiting tumor cell proliferation, which comprises contacting said cells with a tumor cell anti-proliferation effective amount of a compound of formula I or a pharmaceutical composition thereof.

The present invention also provides a method of treating a warm-blooded animal afflicted with a disease in which the inhibition of protein kinase C is of importance which comprises administering to said animal a therapeutically effective amount of a compound of formula I or a pharmaceutical composition thereof.

The present invention further provides a method of treating inflammation in a warm-blooded animal which comprising administering to said animal an anti-inflammatory effective amount of a compound of formula I or a pharmaceutical composition thereof.

The compounds of this invention are novel indolocarbazoles which are isolated along with N-acetylstaurosporine and known indolocarbazoles such as staurosporine from an antibiotic complex produced by cultivating a strain of *Saccharothrix aerocolonigenes* subsp. *copiosa* subsp. nov, SCC 1951, having the identifying characteristics of ATCC 53856 in a pH and temperature controlled aqueous nutdent medium having assimilable sources of carbon and nitrogen under controlled submerged aerobic conditions until a composition of matter having substantial inhibition of myosin light chain kinase ("MLCK") activity is produced.

This invention also provides a process for producing the antibiotic complex of this invention which comprises cultivating an antibiotic complex producing strain of *Saccharothrix aerocolonigenes* subsp. *copiosa* subsp. nov. ATCC 53856 in an aqueous nutrient medium containing assimilable sources of carbon and nitrogen, under submerged aerobic conditions until substantial inhibition of MLCK activity is imparted to said medium and isolating said complex therefrom.

The preferred culture for producing a compound of formula I and the antibiotic complex containing the indolocarbazoles of formula I is a biologically pure culture of the microorganisms *Saccharothrix aerocolonigenes* subsp. *copiosa* subsp. nov having the identifying characteristics of ATCC 53856, said culture being capable of producing an antibiotic complex in a recoverable quantity upon fermentation, under aerobic conditions in an aqueous medium containing assimilable sources of nitrogen and carbon.

DETAILED DESCRIPTION OF THE INVENTION

The indolocarbazole compounds of this invention were isolated from an indolocabazole complex obtained from a culture broth produced by a fermentation under controlled conditions of a biologically pure culture of the microorganism, *Saccharothrix aerocolonigenes* subsp. *copiosa* subsp. nov. SCC 1951, ATCC 53856.

A viable culture of this microorganism has been deposited in the collection of the American Type Culture Collection (ATCC) in Rockville, Md., where it has been assigned accession number ATCC 53856. Should the deposited culture become lost, destroyed or non-viable during the longer of the thirty (30) year period from the date the culture was deposited or the five (5) year period after the last request for the deposited culture or the effective life of the patent which issues from this application the culture will be replaced upon notice by applicants or assignee(s) of this application. Subcultures of *Saccharothrix aerocolonigenes* subsp. *copiosa* subsp.nov. SCC 1951 ATCC 53856 are available during the pendency of this application to one determined by the Commissioner of Patents and Trademarks to be entitled thereto under 37 C.F.R. 1.14 and 35 U.S.C. 122 and will be available to the public without restriction once a patent based on this application is granted. Use of the microorganism is dependent on the U.S. Patent Laws.

DESCRIPTION OF PRODUCING STRAIN

GENERAL METHODS

Source materials used for these studies were frozen ($-80°$ C.) preparations of pure cultures of the microorganism of this invention. Inoculum for the biochemical and physiological tests was prepared by adding 1.0 mL of thawed culture suspension to 10 mL of clear broth in a test tube which was placed on a rotary shaker (300 rpm) at $28°–30°$ C. for 3 to 5 days. The culture was harvested by centrifugation and washed three times with distilled water. The final pellet was resuspended in distilled water to 4 times the packed cell volume. Incubation temperature for the biochemical and physiological tests was $28°$ C. Readings of the results were made at various times up to 21 days for the plate media. Most of the tubed media were read at weekly intervals for 4 to 6 weeks.

MORPHOLOGY

Morphological observations were made on plates of water agar, soil extract agar, glucose-yeast extract agar, nutrient agar and ATCC medium 172. Plates were incubated at $28°$ C. and observed for 2 to 4 weeks.

Strain SCC 1951 was isolated from a soil collected in Spain and is a filamentous organism that forms a well developed, moderately branching substrate mycelium with hyphae approximately 0.4 µm to 0.6 µm in diameter. The vegetative mycelium fragments into coccoid to bacillary elements.

The aerial mycelium consists of very long, sparsely branched hyphae which completely fragment into spores. The spores are smooth walled, cyclindrical and irregular in size (approximately 0.6–0.7 µm wide and 0.9–4.8 µm long). The spore chains are straight to irregularly curved. A few short spore chains of less than 50 spores are usually present but most spore chains contain 50 to 100 spores or more. On many media characteristic clumps of interwoven aerial hyphae or "aerial colonies" are readily observed. No motile elements were present in either the vegetative or aerial mycelium.

CHEMOTAXONOMY

Purified cell wall preparations of SCC 1951 analyzed by the method of Becker [Becker et. al., Appl., Microbiol. 12, 421–423 (1964)] contain the meso-isomer of 2,-6-diaminopimelic acid, alanine, glutamic acid, glucosamine, muramic acid and galactose (Type III). Whole-cell hydrolysates analyzed by the method of Lechevalier [Lechevalier, M. P., J. Lab. Clin. Med. 71, 934–944 (1968)] contain galactose, glucose, mannose, ribose, rhamnose and a trace of madurose. The phospholipids present are diphosphatidylglycerol, phosphatidylinositol, phosphatidylinositol mannosides, phosphatidylethanolamine acylated to both hydroxy and branched chain fatty acids and a minor unknown (Type PII). [Lechevalier et al., Blochem. System. Ecol. 5, 249–260 (1977)]. No mycolates are present. The mole % guanine plus cytosine of the DNA is 71.2% (Tm).

PHYSIOLOGICAL AND BIOCHEMICAL CHARACTERISTICS

The taxonomic procedures were those cited by Gordon [Gordon, R. E., *J. Gen. Microbiol.* 45:355–364 (1966)], Luedemann and Brodsky, Antimicrob. Agents Chemother. 1964, p. 47–52 (1965)] and Horan and Brodsky [Horan and Brodsky, Int. J. Svst. Bacterial., 32:195–200 (1982)]. Physiological characteristics for SCC 1951 are presented in Table I. Acid production for SCC 1951 from carbohydrates is shown in Table II. Growth for *Saccharothrix aerocolonigenes* subsp. *copiosa* SCC 1951, ATCC 53856 occurs at temperatures in the range of about 10° to 40° C. on yeast extract-glucose agar. The optumum growth temperature is about 30° C. to 35° C. Variable growth occurs at 42° C.; no growth was observed at 45° C.

MACROSCOPIC DESCRIPTION OF SCC 1951

All plates were incubated at 28° C. and observed at intervals up to 28 days. The common names for the colors were chosen after comparison with color chips from the ISCC-NBS Centtold Colour Charts, or the Methuen Handbook of Color (Eyre Methuen, London, 1981). The substrate mycelium of SCC 1951 varies from cream to orange yellow to dark yellow brown to brownish black. The aerial mycelium is usually white and tends to be thin. On Czapek sucrose nitrate agar, the white aerial mycelium turns yellow as it ages and becomes moist. The soluble pigments produced vary from yellow to brownish orange to yellow brown. On the carbon utilization medium ISP 9 with trehalose, a reddish orange soluble pigment is present at 7 days. This pigment darkens to brownish orange at 2 to 3 weeks. Results are presented in Table II.

TABLE I

Physiological Characteristics of *Saccharothrix aerocolonigenes* subsp. copiosa SCC 1951, ATCC 53856.

| Test | Results |
| --- | --- |
| Hydrolysis or Decomposition of: | |
| Adenine | − |
| Allantoin | − |
| Casein | + |
| Esculin | + |
| Gelatin | + |
| Guanine | +[1] |
| Hippurate | V |
| Hypoxanthine | + |
| L-tyrosine | + |
| Starch | + |
| Urea | + |
| Xanthine | − |
| Xylan | + |
| Reduction of nitrates to nitrites | + |
| Production of catalase | + |
| Production of phosphatase | + |
| Resistance to lysozyme | + |
| Formation of melanin | − |
| Growth at: 10° C. | + |
| 28° C. | + |
| 35° C. | + |
| 40° C. | + |
| 42° C. | V |
| 45° C. | − |
| Survival at 50° C. for 8 hours | + |

+ = positive; − = negative; V = variable
1 = after incubation for 6 weeks

TABLE II

Acid Production by *Saccharothrix aerocolonigenes* subsp. copiosa SCC 1951, ATCC 53856 from Carbohydrates

| Carbohydrate | Acid Production |
| --- | --- |
| Adonitol | + |
| D-amygdalin | + |
| D-arabinose | + |
| L-arabinose | + |
| D-cellobiose | + |
| Dextrin | + |
| Dulcitol | − |
| i-Erythritol | + |
| D-fructose | + |
| L-fucose | + |
| D-galactose | + |
| Glucose | + |
| Glycerol | + |
| i-Inositol | + |
| Inulin | − |
| Lactose | + |
| Maltose | + |
| D-mannitol | + |
| D-mannose | + |
| D-melezitose | − |
| D-melibiose | + |
| α-methyl-D-glucoside | + |
| α-methyl-D-mannoside | + |
| D-raffinose | − |
| L-rhamnose | + |
| D-ribose | + |
| Salicin | − |
| D-sorbitol | + |
| L-sorbose | + |
| Sucrose | + |
| D-trehalose | + |
| D-xylose | + |

TABLE III

Macroscopic Appearance of *Saccharoxthfix aerocolonigenes* subsp. copiosa SCC 1951, ATCC 53856 on Various Descriptive Media.

| MEDIUM | | RESULTS |
| --- | --- | --- |
| Yeast Extract - | G: | good to excellent |
| Malt Extract Agar | AM: | none to sparse, white |
| (ISP 2) | SC: | sparse |
| | DFP: | variably present; pale yellow-brown |
| | SMP: | yellow-brown |
| Oatmeal Agar | G: | good |
| (ISP 3) | AM: | moderate to abundant, white |
| | SC: | abundant |
| | DFP: | light yellow brown to brownish orange |
| | SMP: | moderate yellowish brown (ISCC-NBS 77) to dark yellowish brown (ISCC-NBS 78) |
| Inogranic Salts - | G: | good |
| Starch Agar (ISP 4) | AM: | sparse to moderate, white, coremia present |
| | SC: | sparse |
| | DFP: | yellow-brown to grayish yellow-brown |
| | SMP: | moderate yellow-brown to dark yellowish brown |
| Glycerol-Asparagine | G: | poor |
| Agar (ISP 5) | AM: | sparse to abundant, white |
| | SC: | moderate to abundant |
| | DFP: | absent |
| | SMP: | translucent - off white to pale yellow-brown |

TABLE III-continued

Macroscopic Appearance of *Saccharoxthfix aerocolonigenes* subsp. copiosa SCC 1951, ATCC 53856 on Various Descriptive Media.

| MEDIUM | | RESULTS |
|---|---|---|
| Water Agar | G: | poor |
| | AM: | none to abundant, white |
| | SC: | none to abundant |
| | DFP: | absent |
| | SMP: | translucent |
| Bennett's Agar | G: | fair |
| | AM: | sparse to moderate, white |
| | SC: | abundant |
| | DFP: | light yellow to pale yellow-brown |
| | SMP: | translucent to moderate yellow (ISCC-NBS 87) |
| Glucose Asparagine Agar | G: | good |
| | AM: | moderate, white, coremia present |
| | SC: | sparse |
| | DFP: | yellow |
| | SMP: | light orange yellow (ISCC-NBS 70) |
| ATCC Medium 172 | G: | excellent |
| | AM: | sparse, white, coremia present |
| | SC: | sparse |
| | DFP: | yellow brown to brownish orange |
| | SMP: | moderate yellowish-brown (ISCC-NBS 77) |
| Czapek-Sucrose Agar | G: | good |
| | AM: | sparse to abundant, white turning yellow, coremia present |
| | SC: | sparce to moderate |
| | DFP: | yellow brown to brownish orange |
| | SMP: | dark orange yellow (ISCC-NBS 72) |
| Glucose-Yeast Extract Agar | G: | good |
| | AM: | none to sparse, white |
| | SC: | moderate to abundant |
| | DFP: | yellow-brown |
| | SMP: | yellow-brown |
| Carbon Utilization Base (ISP 9) with Lactose | G: | excellent |
| | AM: | bloom, white |
| | SC: | absent |
| | DFP: | yellow to yellow-brown |
| | SMP: | cream, turning brownish-black (ISCC-NBS 65) |
| Carbon Utilization Base (ISP 9) with Trehalose | G: | good |
| | AM: | absent |
| | SC: | absent |
| | DFP: | reddish orange (Methuen 7A7) turning brownish orange (Methuen 7C8) |
| | SMP: | brownish orange (Methuen 5C6) |

G = vegetative growth; AM = aerial mycelium; SC = spore chain; DFP = diffusible pigment; SMP = substrate mycelium pigmentation On the basis of the above morphological and chemotaxonomic characteristics, SCC 1951 was placed in the genus Saccharothrix. The description of SCC 1951 was compared with the descriptions of those Saccharothrix species listed on the Approved Lists of Bacterial Names or found in the patent literature: *Saccharothrix australiensis*, *S. espanaensis*., and *S. aerocolonigenes*.

SCC 1951 is easily differentiated from *S. australiensis* and *S. espanaensis*. *S. australiensis* produces melanin, fails to grow on ISP 9 with any carbon source and does not hydrolyze starch or hypoxanthine or produce phosphatase. *S. epanaensis* has a Type PIV phospholipid pattern, strongly hydrolyzes adenine, does not hydrolyze tyrosine and does not produce acid from i-inositol, lactose, mannitol, or melibiose.

The description of SCC 1951, however, closely resembles that of *S. aerocolonigenes* and SCC 1951 was compared directly with *S. aerocolonigene* ATCC 23870, the type strain. SCC 1951 differs from ATCC 23870 in producing acid from erythritol and destroying the chromophore in phenol red. SCC 1951 also produces a reddish orange to brownish orange soluble pigment on carbon utilization medium ISP 9 with trehalose, galactose or ribose as the carbon source. These pigments were never observed on the ATCC 23870 plates.

In a survey of 14 strains of *Saccharothrix* (Nocardia) *aerocolonigenes*, including the type culture of the species, Gordon et. al. (*J. Gen. Microbiol.* 109: 69–78, 1978) found that none produced acid from erythritol. Strain SCC 1951 is a strong producer of acid from erythritol. We, therefore, consider SCC 1951 to be a new subspecies of *Saccharothrix aerocolonigenes* for which we propose the name *Saccharothrix aerocolonigenes* subsp. *copiosa* in reference to the large number of indolocarbazoles produced by this strain.

BIOLOGICAL ACTIVITY OF THE COMPOUNDS OF THIS INVENTION

Protein kinase C (PKC) is a $Ca^{2+}$- and phospholipid-dependent protein kinase involved in mediating a wide variety of cellular responses to growth factors, hormones, oncogenes and other modulators of growth control. Numerous studies have indicated that the enzyme plays a central role in signal transduction and tumor promotion and that this control may occur through one arm of the phosphatidylinositol second messenger system. G. M. Housey et al. (*Cell.*, (1988), Vol. 52, pp. 343–354) have recently shown that the overexpression of a full-length form of PKC ($\beta$1) causes dramatic morphologic and phenotypic changes in fibroblast cell lines consistent with transformation. These studies underscore the critical role of PKC in growth control and tumorigenesis. K. Tamaski et al., [*Biochem. Biophys. Res. Commun.*, (1986), Vol. 135, pp. 397–402] and H. Kase et al., [(1987), ibid. Vol. 142, p. 436–440] disclose that staurosporine and related indolocarbazoles, K252a, and K252b are inhibitory to PKC (from rats' brains) with good potency, in the nanomolar range. Staurosporine has also been shown to inhibit the growth of cells at concentrations which correlate with in vitro PKC inhibition and to have antitumor activity in-vivo.

Indolocarbazoles such as staurosporine have high potency and thus are useful for biological studies but they have limited selectivity against protein kinases. H. Nako et al. [*J. Antibiot.*, (1987) Vol. 40, pp. 706–708] disclose that staurosporine, for example, will inhibit cyclic AMP-dependent protein kinase, myosin light chain kinase (MLCK) and $p60^{v-src}$ tyrosine kinase with similar potencies.

The compounds of this invention are potent inhibitors of PKC with increased selectivity compared to staurospodne as evidenced by comparison of inhibition of PKC to that of MLCK. Staurosporine and K-252a have nanomolar potencies with MLCK to PKC ratios of 1.2 and 1.3 respectively. The compounds of this invention exhibit selective inhibition of MLCK with $IC_{50}$'s in the range of 138 to >1000 nM and PKC with IC50's in the range of 19 to 854 nM and MLCK to PKC ratios 1.2 to 18.8. The PKC was partially purified from rat brain and assayed in the presence of its activators: $Ca^{2+}$, phosphatidylserine and 1-oleoyl-2-acetylglycerol. Histone III-S was used as phosphate acceptor. The MLCK was native enzyme from chicken gizzard fully activated by calmodulin. Kemptamide was used as phosphate acceptor. The compounds with good potency for PKC inhibition as well as selectivity of PKC inhibition relative to other protein kinases indicate in vivo utility as potential antitumor agents.

In agreement with the in vitro kinase activity, the compounds of this invention inhibited (a) serotonin release in human platelets which were prelabelled with [$^3$H] serotonin. Serotonin release from human platelets ($IC_{50}$ ranged from 0.95 to >50 µM) was measured following stimulation for one min. with various doses of thrombin or at various times following addition of 1 unit/ml of thrombin. [T. Tohmatsu et al. *Thrombosis Research*, (1987), Vol. 47, pp. 25–35], (b) phorbol ester induced c-fos expression in cultured mouse BALB/C 3T3 cells which were exposed to the compounds of this invention for 20 hours prior to serum stimulation. The $IC_{50}$'s ranged from 0.6 µM to 5.4 µM. [T. Maniatio et al., "Molecular. Cloning: A Laboratory Manual" (1982), Cold Spring Harbor, N.Y.,] and (c) superoxide release in human neutrophils which were stimulated with either the chemotactic peptide f-met-leu-phe (fMLP) or the phorbol ester, phorbol myristate acetate (PMA). Superoxide release ($IC_{50}$ for fMLP ranged from 0.1 to 9 µM and $IC_{50}$ for PMA ranged from 0.2 to 5 µM) was measured 15 min. after stimulation as superoxide dismutase-inhibitable reduction of cytochrome c. [D. P. Clifford and J. E. Repine, "Methods in Enzymology", (1984), Vol. 105, p. 393 [51].]

The antibiotic complex as well as the individual indolocarbazoles of this invention isolated therefrom were shown to be myosin light chain kinase inhibitors and phosphodiesterase inhibitors and as such have utilation in treating cardiovascular disorders.

H. Kase et al. *J. Antibiot.*[(1986) Vol. 39, pp. 1059–65] disclosed that the indolocarbazole, K-252a lowers blood pressure in SHR and DOC-rats. The indolocarbazoles of this invention lower blood pressure and thus the compounds of this invention exhibit pharmacological activity against cardiovascular disorders and have potent antihypertensive activity.

The compounds of this invention exhibit antimicrobial properties and like K-252 indolocarbazoles exhibit diuretic properties.

THERAPEUTIC USES

The compounds of this invention exhibit selective inhibition of MLCK and PKC and thus exhibit anti-proliferation activity against tumors cells.

Thus, in another aspect, the present invention also provides a method of inhibiting tumor cell proliferation, which comprises contacting said tumor cells with an anti-tumor cell proliferation effective amount of a compound of this invention represented by formula I or a pharmaceutical composition thereof.

In another aspect, the present invention also provides a method of treating a warm-blooded animal afflicted by hypertension which comprises administering to said animal a therapeutically effective amount of a compound represented by formula I sufficient to treat hypertension, or a pharmaceutical composition of a compound represented by formula I.

In still another aspect, the present invention provides a method of treating a warm-blooded animal afflicted with diseases wherein the inhibition of protein kinase C is of importance which comprises administering to said animal a therapeutically effective amount of a compound represented by formula I or a pharmaceutical composition thereof.

D. P. Clifford and J. E. Repine, supra. disclose that inhibition of superoxide indicates anti-inflammatory activity. Compounds of this invention inhibited superoxide release in human neutrophils which had been stimulated with either fMLP ($IC_{50}$ in the range=0.1 to 9 µM) or PMA ($IC_{50}$ in the range=0.2 to 5 µM).

Thus, the present invention provides a method of treating inflammation (arthritis, bursitis, tendonitis, gout as well as other inflammatory conditions) in a warm-blooded animal by administering to such an animal an anti-inflammatory effective amount of a compound of formula I or a pharmaceutical composition thereof.

In yet another aspect, the present invention provides a pharmaceutical composition comprising a compound of this invention represented by formula I or a pharmaceutically acceptable salt thereof, in racemic or optically active form and an inert pharmaceutically acceptable carrier or diluent.

Typical suitable pharmaceutically acceptable salts are acid addition salts formed by adding to the compounds of this invention an equivalent of a mineral acid such as HCl, HF, $HNO_3$, $H_2SO_4$ or $H_3PO_4$ or an organic acid, such as acetic, propionic, oxalic, valeric, oleic, palmitic, stearic, lauric, benzoic, lactic, para-toluenesulfonic, methane-sulfonic, citric, maleic, fumaric, succinic and the like.

The pharmaceutical compositions may be made up by combining the compounds of this invention or a pharmaceutically acceptable salt thereof with any suitable, i.e., inert pharmaceutical carrier or diluent and administered orally, parentally or topically in a variety of formulations.

Examples of suitable pharmaceutical compositions include solid compositions for oral administration such as tablets, capsules, pills, powders and granules, liquid compositions for oral administration such as solutions, suspensions or emulsions. They may also be manufactured in the form of sterile solid compositions which can be dissolved in sterile water, physiological saline or some other sterile injectable medium immediately before use.

It will be appreciated that the actual preferred dosages of the compounds of this invention or pharmaceutically acceptable salts thereof will vary according to the particular compound being used, the particular composition formulated, the mode of application and the particular situs, host and disease being treated. Many factors that modify the action of the drug will be taken into account by the attending clinician, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

The following examples illustrate the claimed invention.

GENERAL METHODS

Solvents, Reagents and Instruments

Solvent used for column chromatography, and high pressure liquid chromatography ("HLPC") were HPLC grade and not redistilled. Water refers to in-house deionized water passed through a Millipore Milli-Q purification system. The CHP-2OP resin was purchased from Mitsubishi. Thin layer chromatography was carried out on Whatman LK6 DF silica gel plates (20×20 cm). Compounds were visualized as a purple spots with 366 nm UV light or by using anisaldehyde spray reagent. High pressure liquid chromatography was carried out using Waters model 510 HPLC pumps controlled by a Waters automated gradient controller. Compounds were monitored at 300 nm using a Hewlett Packard 1040A photodiode array ultraviolet (UV) detector. Ultraviolet spectra were measured on the Hewlett Packard 1040A photodiode array detector or on a Hewlett Packard 8450A UV/Vis spectrophotometer. Infrared spectra were measured on a Nicolet 10-MX instrument. $^1$H and $^{13}$C NMR spectra were measured on a Varian 400 instrument at 400 and 100 mHz, respectively. Assignments were made by comparison with published data. Fast atom bombardment-mass spectra (FAB-MS) were measured on a VG-ZAB-SE double focusing mass spectrometer.

Analytical HPLC

Analytical HPLC was carried out on a YMC $C_{18}$ reverse phase column (120 Å, 5µ, 4.6×150 mm) using a linear gradient of 30–40% aqueous acetonitrile (aq. ACN) over 22 minutes followed by 40% aq. ACN for 8 minutes (flow rate, 1 mL/min). A photodiode arrray-UV detector monitoring at 300 and 220 nm was used to observe the indolocarbazoles.

EXAMPLE 1

The indolocarbazoles of this invention were isolated from an indolocarbazole complex which was produced by fermentation of a biologically pure culture of *Saccharothdrix aerocolonigenes* subsp. *copiosa* subsp. nov. SCC 1951, ATCC 53856.

A. Fermentation

The fermentation, which produces the complex, was started using two or more inoculum stages. Medium for the inoculum stages are listed below. The inoculum and fermentation stages were conducted at a pH from about 6.4 to about 8.5, preferably about 7.0 for the inoculum stage and 7.5 for the fermentation stage.

A temperature of about 27° C. to 35° C. was used to grow the inoculum stages, and to conduct the fermentation stage a temperature of about 27° C.–35° C. was used The media employed were sterilized and cooled prior to inoculation and fermentation in the examples listed below.

Stock cultures were stored as frozen whole broths at sub-zero temperatures.

Inoculum Preparation (First Stage)

Inoculum preparation was carried out in two stages for large scale fermentations (10 L to 100 L). Suitable nutrients for preparing the inocula are listed below:

| Inoculum Medium | |
|---|---|
| Ingredient | g/L |
| Beef extract | 3.0 |
| Tryptone | 5.0 |
| Yeast extract | 5.0 |
| Cerelose | 1.0 |
| Potato starch | 24.0 |
| Calcium carbonate | 2.0 |
| Tap water | 1 L |

Two and a half milliliters of freshly-thawed whole broth were used to inoculate 70 mL of the above-listed inoculum medium in 250 mL Erlenmeyer flasks. The flasks were incubated at 30° C. for 48 hours on a shaker at 300 rpm and having a 2 inch throw.

Second Inoculum Preparation

Twelve 2 L Erlenmeyer flasks containing 500 mL of sterile inoculum medium were inoculated using a 5% inoculum from the first stage. The procedure for the first inoculum stage was followed.

Production (fermentation) Stage

The following fermentation medium has been found to produce the indolocarbazole complex:

| Fermentation Medium | |
|---|---|
| Ingredient | g/L |
| Soluble starch | 15.0 |
| Sucrose | 5.0 |
| Dextrose | 5.0 |
| Soy Peptone | 7.5 |
| Corn steep liquor | 5.0 mL |
| $K_2HPO_4$ | 1.5 |
| NaCl | 0.5 |
| Mineral Solution | * |
| Tap water | 1 L |
| Post sterilization | pH 7.0 |

* 10 mL of a mineral solution containing the following salts in a final concentration (mg/L) of: —$ZnSO_4.7H_2O$, (28); ferric ammonium citrate, (27.8); $CuSO_4.6H_2O$, (1.25); $MnSO_4.H_2O$, (10); $CoCl_2.6H_2O$, (1); $Na_2B_4O_7.H_2O$, (0.88); $Na_2MoO_4.2H_2O$, (0.5).

Five liters of the second stage inoculum were used to inoculate 100L of the fermentation medium. The fermentation was conducted for 66 hours at 30° C. in a 150 L NBS Fermatron with agitation and aeration at 270 rpm and 1.8 cfm, respectively.

No pH adjustment was made to the fermentation but the pH ranged from 6.8 to 7.5 over the course of the 66 hour fermentation.

Production of the complex was monitored over time by HPLC analysis of ethyl acetate extracts of the complex.

B. Isolation of Complex and Separation of the Indolocarbazoles

The culture produced small quantities of a very complex mixture of indolocarbazoles. In an analytical HPLC chromatogram of a partially purified sample of the complex mixture, about 20 indolocarbazole components including N-acetyl staurosporine were detected. The isolation of the indolocarbazole complex was accomplished through a series of silica gel and reverse-phase chromatographies. The individual components were then obtained using size exclusion and reverse-phase semi-preparative HPLC. An exemplary procedure followed for vadous batch sizes is given hereinbelow.

The procedure for a 1000 L batch is described. 1000 L of the fermentation broth was extracted two times with equal volumes of ethyl acetate. The organic solutions were combined and the solvent was removed under vacuum. The resulting oil was then placed on a 25 L silica gel column. The column was eluted with 200 L (4×5 OL) of a 10% methanol in dichloromethane solution followed by 50 L of a 1:1 mixture of methanol and dichloromethane. The active fractions, which were detected by analytical HPLC and exhibited inhibition of myosin light chain kinase, were combined and the solvent was removed. The oil was then subjected to a second silica gel column (6–7 L) using 5% methanol in dichloromethane (v/v) as eluant; 1 L cuts were taken and analyzed as above. The active fractions were then passed through a CHP-20P (IL) reverse-phase column and then eluted with 30, 50, 75 and 100% aq. ACN, the activity was found in the 50 and 75% fractions. The material in the active fractions were subjected to chromatography using a second CHP-20P column using a continuous gradient of 30 to 100% aqueous acetonitdle as solvent to produce partially purified material. The isolation of 2–3 component mixtures were achieved using LH-20 chromatography with 1:1 dichloromethane/acetonitrile as solvent. Twenty-five mL fractions were collected and assayed by analytical HPLC. The final step in purification was semi-preparative HPLC which was carried out on a YMC, $C_{18}$ reverse-phase column (15μ, 120 A, 30×500 mm) using a 30–40% aqueous acetonitrile gradient (UV at 375 nm, 35 mL/min flow rate). From 1000 L batches, the indolocarbazole components (150 mg total) were isolated varying in weight from 1–30 mg including about 20 mg of N-acetyl-staurosporine.

The structures for the indolocarbazoles of this invention were determined by analysis of the following physiochemical data including: UV, MS (high resolution as well as FAB-MS), $^1$H and $^{13}$C NMR and IR spectra and are listed hereinafter as Examples 2–14.

EXAMPLE 2

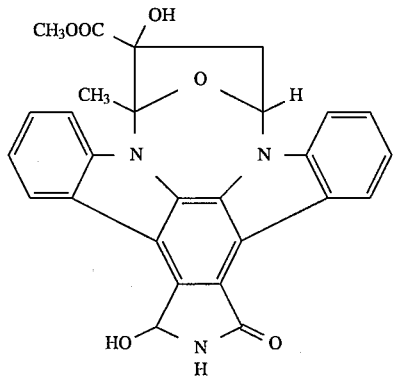

FAB-MS: 484 (M+H), 466 (—H$_2$O), 440, 343, 299, 242

MOLECULAR FORMULA: $C_{27}H_{21}N_3O_6$

UV (MEOH): 207 (35,000), 230 (31,000), 253 (26,000), 270 (sh, 27,000), 281 (sh, 31,000), 292 (55,000), 299 (56,000), 337 (11,000) 353 (10,000), 370 (11,000)

IR (KBR): 3400, 1760, 1720, 1680, 1630, 1580, 1460, 1390, 1360, 1315, 1290, 1270, 1195, 1130, 1070, 740 $^1$H NMR: 9.14 (d, 1H, J=8, H-4), 8.86 (s, 1H, NH), 8.39 (d, 1H, J=9, H-8), (DMSO) 7.92 (d, 1H, J=8.3 , H-11), 7.89 (d, 1H, J=8Hz, H-1), 7.50 (t, 1H, J=8), 7.47 (t, 1H, J=8, H-10), 7.31 (t, 1H, J=8, H-9), 7.27 (t, 1H, J=8, H-3), 7.12 (dd, 1H, J-7, 4.5, H-6'), 6.52 (d, 1H, J=20, 7-OH), 6.42 (d, 1H, J=20, H-7), 6.36 (s, 1H, OH), 3.92 (s, 3H, COOCH$_3$ ), 3.40 (dd, 1H, J=14, 8, H$_β$-5'), 2.02 (dd, J=14, 4.5, H$_α$-5), 2.16 (s, 3H, 2'-Me)

$^{13}$C NMR: 172.8, 170.2, 140.1, 137.0, 135.2, 130.0, 128.6, 125.6, 125.4, (DMSO) 125.1, 124.6, 123.8, 122.9, 122.4, 120.1, 119.6, 118.8(?), 115.5, 115.4, 114.6, 109.1, 99.3, 84.9, 78.5, 52.6, 42.4, 22.8

EXAMPLE 3

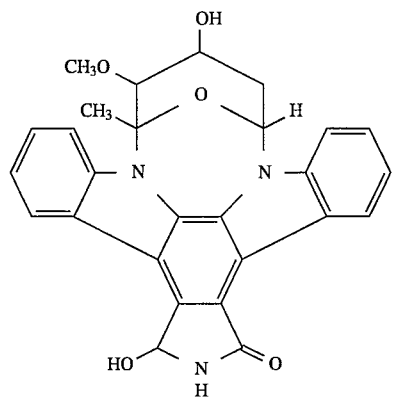

FAB-MS: 470 (M+H)$^+$, 452 425 365 337 310 281, 242

MOLECULAR FORMULA: $C_{27}H_{23}N_3O_5$

UV MEOH): 207 (26,000), 239 (19,000), 292 (sh, 24,000), 301 (30,000), 330 (7,000), 358 (6,000), 375 (6,000)

IR (KBR): 3400, 1680, 1455, 1350, 1315, 1115, 1020, 745

$^1$H NMR: 9.20 (d, 1H, J=8, H-4), 8.70 (s, 1H, NH), 8.34 (d, 1H, J=8, H-8), 7.98 (d, 1H, J=8, H-11), 7.58 (d, 1H, J=8, H-1), 7.46 (t, 1H, J=7.5, H-2), 7.38 (t, 1H, J=7.8, H-10), 7.28 (t, 1H, J=7.6, H-3), 7.26 (t, 1H, J-8, H-9), 6.76 (d, 1H, J=5.5, H-6'), 7.40 (d, 1H, J=10, 7-OH), 7.32 (d, 1H, J=10, H-7), 4.26 (m, 1H), 4.18 (d, 1H, J=3, OH), 3.80 (d, 1H, J=2.5, H-3), 3.41 (s, 3H, OMe), 2.58 (m, 1H, H$_β$-5), 2.41 (m, 1H, H$_α$-5), 2.30 (s, 1H, 2'-Me)

$^{13}$C NMR: 170.6, 139.8, 136.3, 134.2, 129.6, 125.3, 124.9, 124.2, 123.4, 122.4, 122.3, 119.2, 119.0, 117.8, 115.4, 114.4, 113.6, 108.6, 90.7, 82.2, 79.4, 78.4, 58.7, 56.3, 33.7, 29.8

EXAMPLE 4

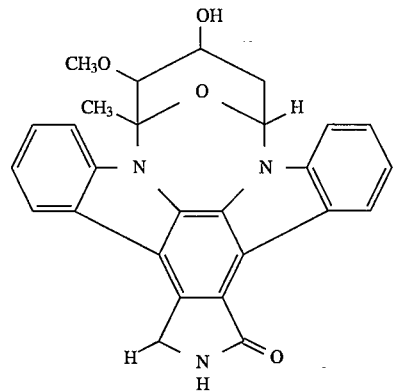

FAB-MS: 454 (M+H), 366, 323, 311, 295

HR-MS EXACT MASS: (M+H)$^+$ FOUND: 454.1740 CALCULATED: 454.1769

MOLECULAR FORMULA: $C_{27}H_{23}N_3O_4$

UV (MEOH): 205, (30,000), 238 (sh, 20,000), 244 (sh, 19,000) 265 (sh, 19000), 292 (40,000), 321 (8,000), 336 (9,000), 355 (7,000), 373 (8,000)

IR (KBR): 3400, 3280, 1685, 1630, 1585, 1360, 1350, 1275, 1230, 1150, 1110, 1020, 1010, 740

$^1$H NMR: 9.34 (d, 1H, J=8.0, H-4), 7.96 (d, 1H, J=7.8), 7.88 (d, 1H, (CDCl$_3$) J=7.3), 7.46 (t, 1H, J=7.1), 7.41 (t, 1H, J=7.1), 7.40 (t, 1H, J=7.3), 7.35 (t, 1H, J=7.4), 7.20 (d, 1H, J=7.8), 6.57 (d, 1H, J=5.13, H-6'), 6.17 (s, 1H, NH), 4.73 (AB, J=17, H$_2$-7), 4.43 (m, 1H, H-4'), 3.73 (d, 1H, J=2.9, H-3'), 3.60 (s, 3H, 3'-OMe), 2.80 (dd, 1H, J=14.6, 3, H$_\beta$-5'), 2.51 (m, 1H, H$_\alpha$-5'), 2.34 (s, 3H, 2'-Me), 2.29 (s, 1H, OH)

$^{13}$C NMR: 172.1, 139.6, 131.9, 129.4, 126.1, 125.4, 124.6, 124.0, 123.8, 122.5, 120.5, 119.5, 118.8, 118.5, 115.6, 114.0, 113.4, 108.5, 90.8, 82.2, 79.4, 58.7, 56.4, 45.3, 33.8, 29.8

EXAMPLE 5

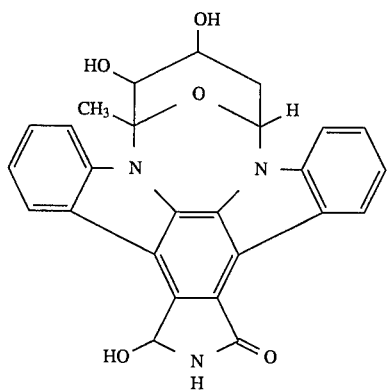

FAB-MS: 456 (M+H)$^+$, 438 (—H$_2$O) 391, 309

HR-MS EXTRACT MASS: (M+H)$^+$ FOUND: 456.1532 CALCULATED: 456.1559

MOLECULAR FORMULA: C$_{26}$H$_{21}$N$_3$O$_5$

UV (MEOH): 208 (24,000), 239 (15,000), 292 (sh, 20,000), 301 (27,000) 340 (sh, 4,000), 358 (4,000), 376 (4,000)

IR (KBR): 3400, 1690, 1640, 1580, 1450, 1350, 1320, 1150, 1120, 1025, 750

$^1$H NMR: 9.23 (d, 1H, J=7.6, H-4), 8.74 (s, 1H, NH), 8.37 (d, 1H, (DMSO) J=7.0), 8.07 (d, 1H, J=7.5), 7.59 (d, 1H, J=8.3), 7.46 (t, 1H, J=8.1, 7.1), 7.38 (t, 1H, J=8.4, 7.1), 7.27 (t, 1H, J=8.0, 7.1), 7.24 (t, 1H, J=8.3, 7.1), 6.74 (d, 1H, J=4.9, H-6'), 6.43 (d, 1H, J=10.5, 7-OH), 6.36, (d, 1H, J=10.5 , H-7), 5.45 (d, 1H, J=7.1, H-3'), 4.10 (m, 2H, OH), 3.96 (m, 1H, H-4'), 2.63 (1H, m, H-5'), 2.40 (dd, 1H, H-5'), 2.27 (s, 3H, 2'-Me)

$^{13}$C NMR: 170.6, 140.1, 136.4, 134.2, 129.7, 126.9, 125.2, 124.9, 124.2, (DMSO) 123.4, 122.4, 119.2, 118.9, 118.0, 117.8, 115.6, 114.5, 113.6, 108.5, 92.2, 79.3, 78.4, 63.9, 48.5, 34.2, 29.7

EXAMPLE 6

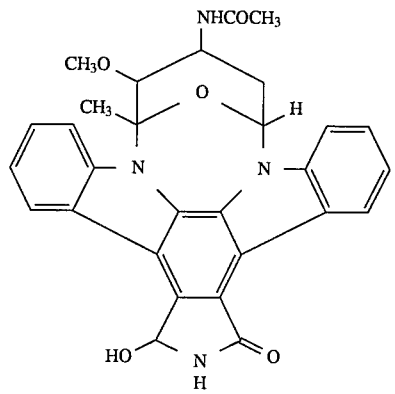

FAB-MS: 511 (M+H)$^+$, 493, 364, 299

HR-MS EXACT MASS: (M+H)$^+$ FOUND: 511.2008 CALCULATED: 511.1981

MOLECULAR FORMULA: C$_{29}$H$_{26}$N$_4$O$_5$

UV (MEOH): 206 (40,000), 238 (29,000), 293 (sh, 43000), 300 (54,000), 325 (sh, 10,000), 339 (sh, 9,000), 357 (8,000), 374 (9,000)

IR (KBR): 3390, 3360, 1680, 1635, 1580, 1450, 1340, 1320, 1120, 1020, 740

$^1$H NMR: 8.7 (d, 1H, J=8.0, H-4), 8.64 (d, 1H, J=7.0, H-8), 7.68 (d, 1H, (CDCl$_3$) J=7.4 Hz, 7.4 (t, 1H, J=7.0), 7.35 (t, 1H, J=7.6), 6.90 (d, J=3.9, 2H), 6.55–6.7 (m, 4H), 4.7 (d, 1H, J=6.1, H NCOCH$_3$ ), 4.38 (m, 1H, H-4'), 3.7 (d, 1H, J=4.3, H-3'), 3.08 (s, 3H, —OCH$_3$), 2.75 (1H, H-5'), 2.47 (s, 3H, CH$_3$), 2.38 (m, 1H, H-5'), 0.6 (s, 3H, COCH$_3$)

$^{13}$C NMR: 173.1, 169.9, 139.8, 135.8, 133.7, 128.0, 125.6, 125.4, 125.1

(CDCl$_3$) 124.8, 123.9, 123.7, 122.1, 120.6, 120.0, 117.7, 116.1, 114.9, 114.2, 107.2, 90.8, 81.5, 80.2, 57.3, 40.5, 30.3, 29.9, 22.2

EXAMPLE 7

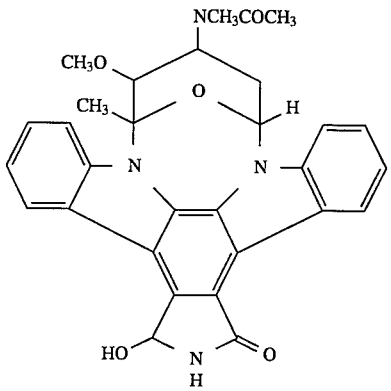

FAB-MS: 525 (M+H)$^+$, 507, 410, 393, 364, 337

MOLECULAR FORMULA: C$_{30}$H$_{28}$N$_4$O$_5$

UV (MEOH): 206 (31,000), 238 (21,000), 293 (sh, 31,500), 300 (37,000), 340 (6,600), 356 (6,000), 374 (6,000)

IR (KBR): 3400, 1690, 1660, 1460, 1350, 1320, 1120, 1020, 740

$^1$H NMR: 8.8, (d, 1H, J=8.1, H-4), 8.62 (d, 1H, J=7.8, H-8), 7.51 (d, 1H, (CDCl$_3$) J=7.8), 7.4 (td, 1H, J=8.0 1.4), 7.35 (dd, 1H, J=8.0,1.0), 7.04 (t, 1H, J=7.6), 6.8 (d, 1H, J=8.1, H-1), 6.7 (brs, 1H, N$\underline{H}$), 6.72 (d, 1H, J=7.0, H-6'), 6.51 (dd, 1H, J=12.4, 1.0, H-7), 5.32 (d, 1H, J=12.8, 7-O$\underline{H}$), 4.93 (m, 1H, J=13.5, 1.2, H-4'), 3.7 (s, 1H, H-3'), 2.7 (s, 3H, OMe), 2.4 (s, 3H, Me), 2.4 (H-5'), 2.27 (ddd, 1H, J=12.9, 12.9, 3.5, H-5'), 2.1 (s, 3H, NCH$_3$), 1.6 (s, 3H, NCOCH$_3$)

$^{13}$C NMR: 170.3, 168.8, 138.8, 136.5, 134.5, 129.3, 126.1, 125.4, 125.0, (DMSO) 123.5, 123.3, 122.3, 119.9, 119.4, 115.9, 114.9, 114.4, 108.8, 93.2, 81.7, 81.2, 78.4, 60.1, 43.7, 29.1, 28.8

EXAMPLE 8

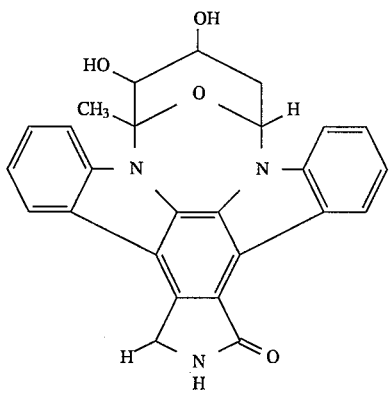

FAB-MS: 440 (M+H)$^+$, 366, 311, 293, 291

MOLECULAR FORMULA: C$_{26}$H$_{21}$N$_3$O$_4$

UV (MEOH): 206 (30,000), 238 (22,000), 263 (sh, 20,000), 293 (40,000) 319 (11,000), 337 (10,000), 357 (7,000), 373 (8,000)

IR (KBR): 3410, 1660, 1450, 1350, 1320, 1150, 1110, 1010, 740

$^1$H NMR: 9.38 (d, 1H, J=7.4 Hz, H-4), 8.50 (brs, 1H, N$\underline{H}$), 8.09 (d, 1H, J=8.5), 7.95 (d, 1H, J=6.9), 7.59 (d, 1H, J=8.1), 7.45 (td, 1H, J=7.7, 1.0), 7.40 (td, 1H, J=8.5, 1.0), 7.27 (td, 2H, J=7.5), 6.76 (d, 1H, J=5.1, H-6'), 5.45 (d, 1H, J=7.1, OH), 4.93 (AB, 2H, J=17 Hz, H-7), 4.1 (m, 2H), 3.98 (m, 1H), 2.62 (m, 1H, J=15, H-5'), 2.38 (m, 1H, J=15, 3, H-5'), 2.3 (s, 3H, 2'-Me)

$^{13}$C NMR: 172.1, 139.8, 136.0, 132.0, 129.4, 126.2, 125.4,125.4, 124.6, 124.0, 123.8, 122.5, 120.6, 119.5, 118.8, 118.5, 115.7, 114.0, 108.4, 92.2, 79.2, 63.9, 57.6, 45.3, 34.3, 29.6

EXAMPLE 9

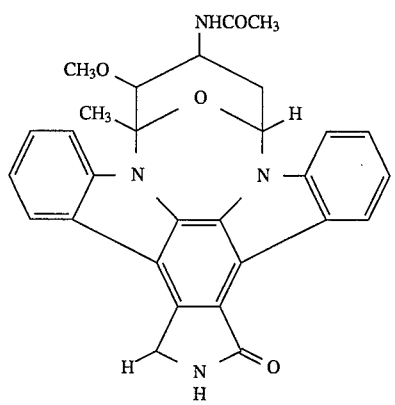

FAB-MS: 495 (M+H)$^+$, 394, 362, 348, 338

HR-MS EXACT MASS: (M+H) FOUND: 495.1996 CALCULATED: 495.2032

MOLECUIAR FORMULA: C$_{29}$H$_{26}$N$_4$O$_4$

UV (MEOH): 204 (34,000), 237 (sh, 25,000), 243 (25,000), 264 (sh, 25000), 291 (54,000), 319 (12,000), 334 (14,000), 354 (9,000), 372 (10,000)

IR (KBR): 3420, 3320, 1680, 1635 (sh), 1455, 1340, 1315, 1270, 1225, 1120, 1020, 760, 740

$^1$H NMR: 9.4 (d, 1H, J=7.9 Hz, H-4), 7.98 (d, 1H, J=8.6), 7.94 (d, 1H, (CDCl$_3$) J=8.8), 7.50 (td, 1H, J=6.9, 1.2), 7.48 ( td, 1H, J=7.0, 1.4), 7.39 (td, 2H, J=7.9, 1.0), 7.27 (d, 1H, J=8.3), 6.60 (d, 1H, J=4.4, H-6'), 6.50 (s, 1H, NH), 5.17 (d, 1H, J=6.1, N—H), 5.05 (AB, 2H, H$_2$-7), 4.60 (m, 1H, H-4'), 3.91 (d, 1H, J=4.4, H-3'), 3.41 (s, 3H, 3'-OMe), 3.09 (ddd, 1H, J=15, 3.9, 1.2, H-5'), 2.53 (ddd, 1H, J=14.9, 5.6, 4.2, H-5') 2.38 (s, 3H, 2'-Me), 0.80 (s, 3H, COCH$_3$)

$^{13}$C NMR: 173.3, 170.2, 140.0, 136.8, 132.2, 128.3, 126.6, 125.9, 125.3, (CDCl$_3$) 125.0, 124.7, 123.2, 121.0, 120.9, 120.4, 119.4, 116.2, 115.6, 114.7, 107.6, 91.3, 81.3, 80.2, 57.2, 46.0, 40.6, 30.7, 29.8, 22.4

EXAMPLE 10

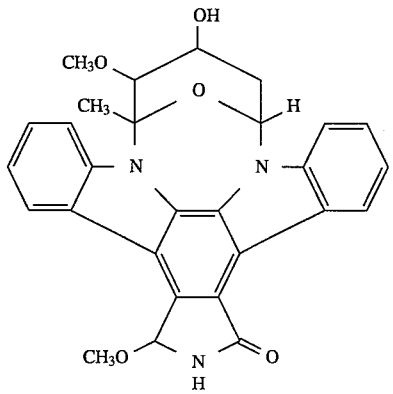

FAB-MS: 484 (M+H)$^+$, 452 (-MeOH), 425, 396, 364, 336, 309, 281

HR-MS EXACT MASS: (M+H) FOUND: 484.1854 CALCULATED: 484.1872

MOLECULAR FORMULA: C$_{28}$H$_{26}$N$_3$O$_5$

UV (MEOH): 208 (29,000), 239 (25,000), 293 (sh, 36,000), 301 (49,000), 340 (75,000), 359 (7,000), 375 (8,000)

IR (KBR): 3390, 1690, 1680, 1650, 1630, 1450, 1350, 1325, 1115, 1090, 1055 745

$^1$H NMR: 9.21 (d, 1H, J=8.0, H-4), 8.93 (brs, 1H, NH), 8.22 (d, 1H, J=7.5, (DMSO) H-8), 8.00 (d, 1H, J=8.5, H-11), 7.61 (d, 1H, J=8.2, H-1), 7.50 (t, 1H, J=7.3, H-2), 7.41 (t, 1H, J=7.3, H-10), 7.31 (t, 1H, J=7.4, H-3), 7.27 (t, 1H, J=7.3, H-9), 6.78 (d, 1H, J=4.7, H-6'), 6.45 (brs, 1H, H-7), 4.27 (m, 1H, H-4'), 4.20 (d, 1H, J=2.9, OH), 3.83 (d, 1H, J=2.4, H-3'), 3.43 (s, 3H, 3'-OMe), 3.22 (s, 3H, 7-OMe), 2.60 (m, 1H, H-5'), 2.40 (m, 1H, H-5'), 2.31 (s, 3H, 2'-Me)

$^{13}$C NMR: 171.2, 140.0, 136.4, 130.3, 129.6, 127.2, 125.2, 125.1, 124.4, (DMSO) 123.3, 122.2, 121.8, 119.4, 118.6, 115.6, 114.5, 113.8, 108.7, 90.8, 84.1, 82.2, 79.5, 58.6, 56.4, 151.0, 33.6, 29.8

EXAMPLE 11

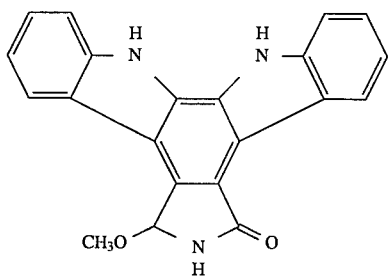

FAB-MS: 342 (M+H)$^+$, 310, 283, 255

MOLECULAR FORMULA: $C_{21}H_{15}N_3O_2$

UV (MEOH): 206 (24,000), 234 (23,000), 252 (sh, 33,500), 296 (45,600), 332 (8,000), 344 (6,500), 361 (4,700)

IR (KBR): 3250, 1670, 1650, 1580, 1450, 1405, 1290, 1020, 1000, 760

$^1$H NMR: 11.0 (s, 1H, NH), 10.7 (s, 1H, NH), 9.26 (d, 1H, H-4), 8.38 (d, 1H), 7.2–7.8 (m, 6H), 6.54 (s, 1H, H7), 3.20 (s, 3H, OMe)

$^{13}$C NMR: 171.4, 139.4, 139.2, 131.3, 128.0, 126.3, 125.3, 125.2, 123.4, 122.4, 122.2, 122.0, 119.8, 119.1, 118.7, 115.1, 114.8, 111.7, 11.4, 84.2, 51.1

EXAMPLE 12

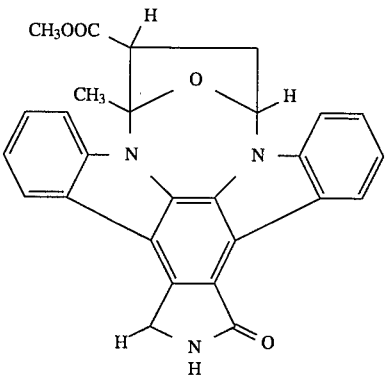

FAB-MS: 452 (M+H)$^+$, 368, 337, 311, 253

MOLECULAR FORMULA: $C_{27}H_{21}N_3O_4$

UV (MEOH): 206 (27,000), 230 (21,000), 243 (sh, 19,000), 267 (sh, 21,000), 281 (sh, 30,000), 290 (44,000), 321 (sh, 9,000), 334 (11,000), 352 (8,000), 370 (9,000)

IR (KBR): 3410, 1740, 1690, 1670, 1630, 1460, 1450, 1310, 1270, 1145, 1125, 1110, 740

$^1$H NMR: 9.42 (d, 1H, H-4), 7.90 (d, 1H), 7.65 (d, 1H), 7.2–7.6 (m, 5H, ar), 7.02 (d, 1H, H-5'), 6.5 (br s, 1H, NH), 4.97 (s, 2H, H$_2$-7), 4.30 (s, 1H), 3.75 (dd, 1H, H-4'), 3.45 (s, 3H, COOCH$_3$), 2.83 (d, H-4'), 2.34 (s, 3H, 2'-Me)

EXAMPLE 13

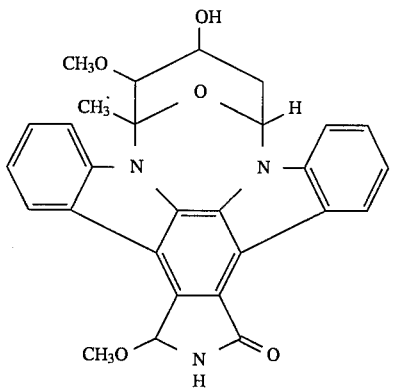

FAB-MS: 484 (M+H)$^+$, 452, 364, 309, 281, 255

HR-MS EXACT MASS: (M+H) FOUND: 484.1845 CALUATED: 484.1972

MOLECULAR FORMULA: $C_{28}H_{26}N_3O_5$

UV (MEOH): 207 (28,000) 239 (24,000), 292 (SH, 34,000), 301 (44,000), 336 (sh, 7,000), 357 (6,000), 376 (7,000)

$^1$NMR: 9.35 (d, 1H, J=7.6, H-4), 8.44 (d, lB, J=7.8, H-8), 7.91 (d, (CDCl$_3$) J=8.5, H-11), 7.51 (t, 1H, J=7.2), 7.45 (t, 1H, J=7.0), 7.36 (t, 1H, J=7.1), 7.32 (t, 1H, J=7.1), 7.26 (d, 1H, J=8.1, H-1), 6.59 (d, 1H, J=1.3 Hz, H-7), 6.57 (d, 1H, J=4.4, H-6'), 6.29 (s, 1H, NH), 4.39 (m, 1H, H-4'), 3.72 (d, 1H, J=2.9, H-3'), 3.56 (s, 3H, 7-OMe), 3.05 (s, 3H, 3'-OMe), 2.76 (dd, 1H, J-15, 4, H-5'), 2.50 (m, 1H, H-5'), 2.34 (s, 3H, 2'-Me)

$^{13}$C NMR 171.7, 140.3, 137.0, 130.0, 129.8, 127.2, 126.6, 125.7, 124.8, (CDCl$_3$) 124.1, 123.1, 122.8, 120.4, 120.2, 119.3, 115.6, 115.3, 107.3, 90.6, 84.1, 83.0, 79.3, 60.3, 57.4, 49.7, 33.3, 30.2

EXAMPLE 15
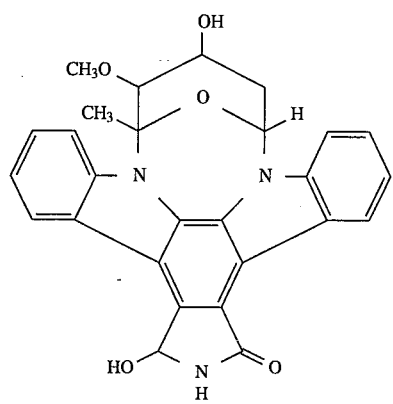
FAB-MS: 470 (M+H)⁺, 452, 425, 382, 365, 337, 310, 283, 255
MOLECULAR FORMULA: $C_{27}H_{23}N_3O_5$
UV (MEOH): 207, 239, 292, 300, 330, 358, 375
$^1$H NMR: 9.25 (d, 1H), 8.33 (d, 1H), 7.77 (d, 1H)
(CDCl$_3$) 7.53 (t, 1H), 7.3 (t, 2H), 7.2 (t, 1H) 6.4 (d, 1H), 6.3 (1H), 6.29 (1 H), 4.0 (d, 1H), 3.8 (d, 1H), 3.6 (1 H), 3.53 (s, 3H) 2.3 (s, 3H), 2.2 (1 H), 1.8 (1 H)
These indolocarbazole of the Example is probably a C-7 isomer of the indolocarbazole of Example 3.
What is claimed is:
1. A compound selected from one represented by the formulas A to F and H to K:
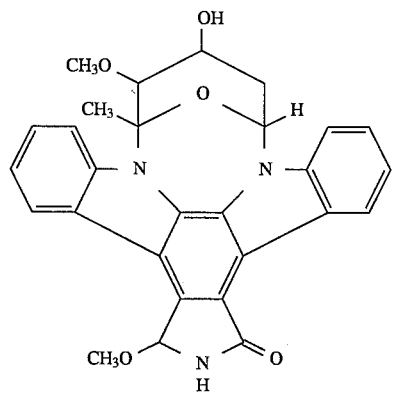
A
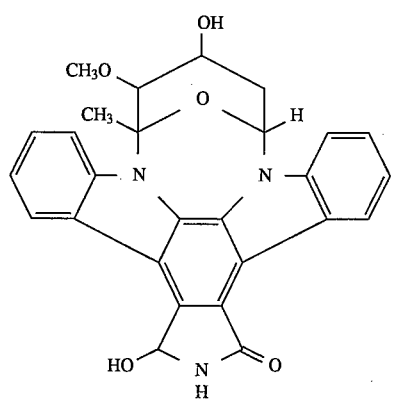
B
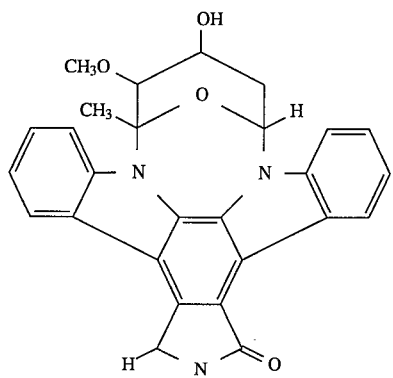
C
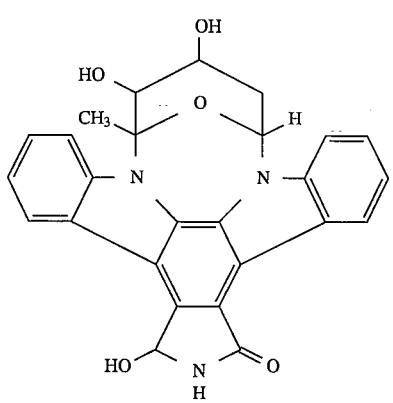
D
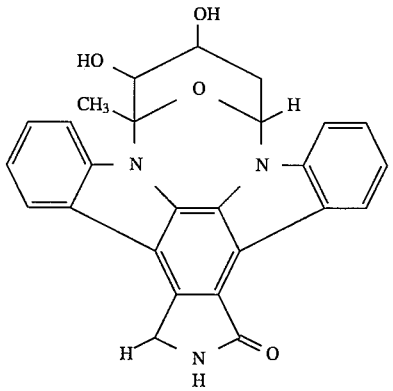
E
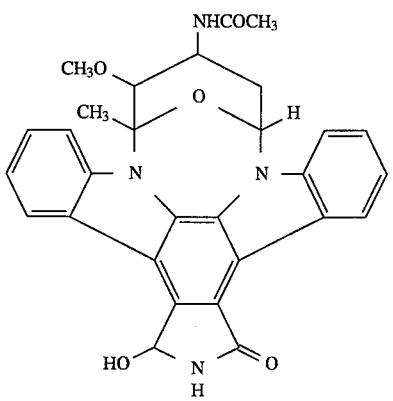
F

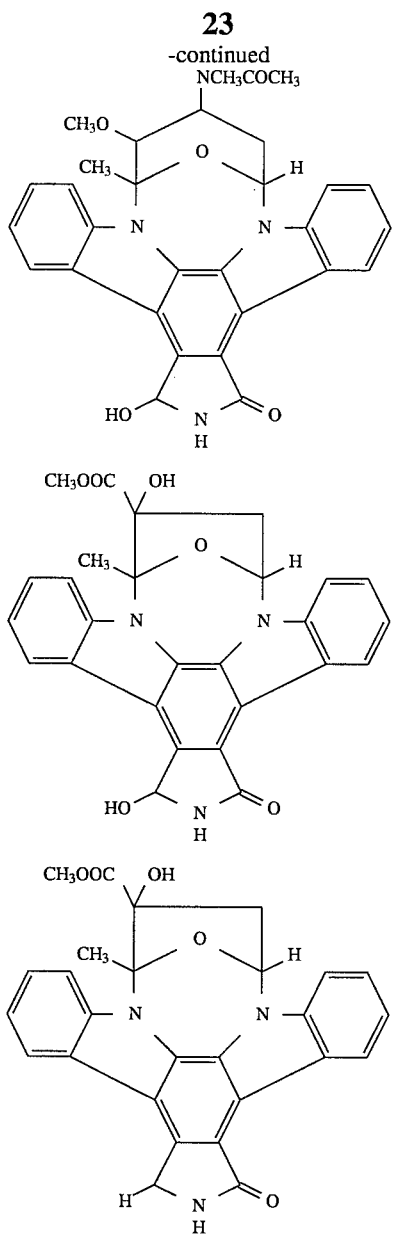

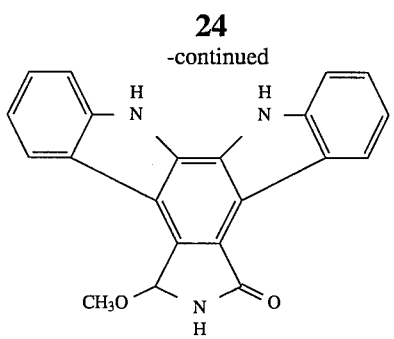

2. A compound of claim 1 which is represented by formulas A to H.

3. A compound of claim 2 which is represented by formula H.

4. A pharmaceutical composition comprising a therapeutically effective amount of a compound of claim 1 and a pharmaceutically acceptable carrier.

5. A pharmaceutical composition of claim 4 comprising a therapeutically effective amount of a compound of formula I useful in warm-blooded animals for inhibiting myosin light chain kinase or protein kinase C or tumor cell proliferation or for producing an anti-hypertensive effect or an anti-inflammation effect.

6. A method of treating a warm-blooded animal afflicted by hypertension, which comprises administering to said animal a therapeutically effective amount of a compound of claim 1 or a pharmaceutical composition thereof sufficient to treat hypertension.

7. A method of inhibiting tumor cell proliferation, which comprises contacting said cells with a tumor cell anti-proliferation effective amount of a compound of claim 1 or a pharmaceutical composition thereof.

8. A method of treating a warm-blooded animal afflicted with a disease wherein the inhibition of protein kinase C is of importance which comprises administering to said animal an amount of a compound of claim 1 or a pharmaceutical composition thereof therapetrically effective for such treating.

9. A method of treating. inflammation in a warm-blooded animal which comprises administering to said animal an anti-inflammatory effective amount of a compound of claim 1 or a pharmaceutical composition thereof.

* * * * *